(12) United States Patent
Alanko et al.

(10) Patent No.: US 12,326,268 B2
(45) Date of Patent: Jun. 10, 2025

(54) METHOD OF MEASURING THE HEALTH OF A HOUSE

(71) Applicant: IISY OY, Espoo (FI)

(72) Inventors: Antti-Jaakko Alanko, Espoo (FI); Bindhya Vashini Tiwari, Espoo (FI); Antti Alaluusua, Espoo (FI)

(73) Assignee: ISY OY, Espoo (FI)

( * ) Notice: Subject to any disclaimer, the term of this patent is extended or adjusted under 35 U.S.C. 154(b) by 290 days.

(21) Appl. No.: 17/778,709

(22) PCT Filed: Nov. 23, 2020

(86) PCT No.: PCT/EP2020/083070
§ 371 (c)(1),
(2) Date: May 20, 2022

(87) PCT Pub. No.: WO2021/099637
PCT Pub. Date: May 27, 2021

(65) Prior Publication Data
US 2023/0003410 A1    Jan. 5, 2023

(30) Foreign Application Priority Data
Nov. 22, 2019   (FI) .................................. 20196006

(51) Int. Cl.
*F24F 11/63*   (2018.01)
*F24F 11/49*   (2018.01)
(Continued)

(52) U.S. Cl.
CPC .............. *F24F 11/63* (2018.01); *F24F 11/49* (2018.01); *F24F 11/52* (2018.01); *F24F 11/56* (2018.01);
(Continued)

(58) Field of Classification Search
CPC .. F24F 11/63; F24F 11/49; F24F 11/52; F24F 11/56; F24F 11/58; F24F 2110/10;
(Continued)

(56) References Cited

U.S. PATENT DOCUMENTS

| | | |
|---|---|---|
| 2013/0174646 A1 | 7/2013 | Martin |
| 2015/0369505 A1 | 12/2015 | Malve et al. |

(Continued)

FOREIGN PATENT DOCUMENTS

| | | | | |
|---|---|---|---|---|
| CN | 110 410 931 | | 11/2019 | |
| EP | 2 944 888 | | 11/2015 | |
| FR | 2945335 | A1 * | 11/2010 | ........... F24F 11/0001 |
| WO | 2016/148651 | | 9/2016 | |
| WO | WO-2020055872 | A1 * | 3/2020 | .............. F24F 11/30 |

OTHER PUBLICATIONS

FR-2945335-A1, English Translation (Year: 2010).*
(Continued)

*Primary Examiner* — Ryan D Walsh
(74) *Attorney, Agent, or Firm* — NIXON & VANDERHYE

(57) ABSTRACT

Disclosed are methods for measuring building health index using some mandatory and set of optionally configured parameters and utilizing building monitoring system having a connection to sensors in or pertaining to a building, and including central computing environment and one or more display devices showing the measurement. A building utilizing this method may be installed with one or more sensors, and which may be communicating to a locally installed communication device or a centrally installed computing environment that can collect the measurements over a period.

20 Claims, 5 Drawing Sheets

(51) Int. Cl.
    *F24F 11/52*     (2018.01)
    *F24F 11/56*     (2018.01)
    *F24F 11/58*     (2018.01)
    *F24F 110/10*     (2018.01)
    *F24F 110/40*     (2018.01)
    *F24F 110/70*     (2018.01)
    *G01N 33/00*     (2006.01)

(52) U.S. Cl.
    CPC .......... *F24F 11/58* (2018.01); *G01N 33/0027* (2013.01); *G01N 33/0075* (2013.01); *F24F 2110/10* (2018.01); *F24F 2110/40* (2018.01); *F24F 2110/70* (2018.01); *G05B 2219/2614* (2013.01)

(58) Field of Classification Search
    CPC .............. F24F 2110/40; F24F 2110/70; G01N 33/0027; G01N 33/0075; G05B 2219/2614
    See application file for complete search history.

(56) References Cited

U.S. PATENT DOCUMENTS

| | | | |
|---|---|---|---|
| 2016/0231014 A1 | 8/2016 | Ro et al. | |
| 2018/0299150 A1* | 10/2018 | Ajax | F24F 11/0008 |
| 2019/0056132 A1* | 2/2019 | Warren | F24F 11/62 |
| 2019/0353379 A1* | 11/2019 | Lee | F24F 11/50 |
| 2021/0103260 A1* | 4/2021 | Khurana | G05B 23/0237 |
| 2021/0258660 A1* | 8/2021 | Stamatakis | F24F 11/30 |

OTHER PUBLICATIONS

WO-2020055872-A1, English Translation (Year: 2020).*
International Search Report for PCT/EP2020/083070 dated Feb. 25, 2021, 4 pages.
Written Opinion of the ISA for PCT/EP2020/083070 dated Feb. 25, 2021, 6 pages.

* cited by examiner

METHOD OF MEASURING THE HEALTH OF A HOUSE

This application is the U.S. national phase of International Application No. PCT/EP2020/083070 filed Nov. 23, 2020 which designated the U.S. and claims priority to FI 20196006 filed Nov. 22, 2019, the entire contents of each of which are hereby incorporated by reference.

FIELD OF THE INVENTION

Generally, the present invention relates to computer-implemented indoor air quality measurement systems and methods. Particularly, however not exclusively, the invention pertains to a computer-implemented system and method for measuring the health of a real estate in relation to indoor air quality.

BACKGROUND

In many countries, buildings have standards and guidelines for measuring indoor air quality to assess and protect the health and wellbeing of the occupants of the building. People are spending more time indoors and technical functionalities of the indoor building have grown complex. There are various factors that can contribute to the air quality consisting of technical factors like design of the building and wrong adjustments of heating- and ventilation systems that can lead to issues in temperature, moisture, ventilation and pressure differentials of the building. In addition, incorrectly working building can lead to the presence of indoor air pollutants e.g. PM10, PM2.5, CO, CO2, HCHO, TVOC, bacteria, fungi, SO2, and NO2 also contribute to indoor air quality. Even though these indoor air pollutants and poor ventilation or moisture can cause only slight discomfort in health to human body without threat of life, the possibility of chronic illnesses or cancer could be increased if people are exposed under the polluted air with lower concentration of emission in the long term.

Technical malfunctioning of the structural and mechanical factors contribute to how the indoor air quality is perceived and the effectiveness and general wellbeing of people inside it.

Interpretation of indoor air quality in relation to several factors like moisture, temperature, pressure differential, and presence of air pollutants require measuring each of these parameters individually and making a general conclusion with expertise and knowledge required by humans to judge on the air quality. In addition, even if the quality of indoor air can be measured by several sensors available in the industry, there is not yet a defined mechanism how to use it for measuring building health index.

Some prior art solutions presented in patent publications include US 2013174646 A1, which discloses a monitoring system that uses data points to form a residence-specific fingerprint for a building with the goal of monitoring especially indoor air comfort and air quality safety for people. US 2016231014 A1 discloses a system for managing environmental conditions inside a building wherein the system may compute a comfort level or productivity level score corresponding to the environmental condition in the structure based upon the received environmental data and facilitate control of the HVAC systems in the building to adjust conditions in the building. CN 110410931 A discloses a system particularly for measuring indoor air quality and facilitating control and regulation of the indoor air quality. US 2015369505 A1 discloses another solution for controlling indoor air quality.

SUMMARY OF THE INVENTION

The objective of the embodiments of the present invention is to at least alleviate one or more of the aforementioned drawbacks evident in the prior art particularly in the context of building condition monitoring. The objective is generally achieved with a computer-implemented method and system in accordance with the claims.

The present invention comprises a method for measuring the health status of a building using health monitoring system that uses parameters measured by at least one or more sensors installed into a building, measuring at least room temperature, Carbon-di-oxide and differential pressure, and optionally one or more parameters, that the system may be configured to measure. The monitoring system uses these parameters measured by the sensors and sent over a network communication system to determine the health status of the building over a measurement window, which health status may be further displayed over one or more user interfaces. The advantage of the calculated health index and other individual measured parameters is that it may give the information how the building health is developing in a simple format that may be used to decide technical functioning of ventilation, heating, building health and risks caused by building users.

The present invention focuses particularly on a method for collecting data over a period of time from a multiple different sensors pertaining to building and using the collected data to calculate an index indicating the health of the building, and not necessarily any current state of conditions in said building. The calculated index is comparable with other buildings and its use for measuring the functioning of the building, which may be used to determine whether the building needs fixing, which is different from real-time environment comfort monitoring and adjustment.

Examples of technical effect of the present solution in relation to prior art include index calculation methodology that is comparable so that different building may be compared in how they function and how their function develops over time, which may be used e.g. for deciding when a building needs renovation. This is a different aim and use of the method when compared to the prior art as the cited documents commonly refer to monitor indoor air quality for optimization and control purposes with an aim for real-time environment comfort for users.

The expression "a number of" may herein refer to any positive integer starting from one (1). The expression "a plurality of" may refer to any positive integer starting from two (2), respectively.

Different embodiments of the present invention are also disclosed in the attached dependent claims.

LIST OF ABBREVIATIONS

PM10 Particulate matter 10 micrometers or less in diameter
PM2.5 Particulate matter 2.5 micrometers or less in diameter
O3 Ozone
CO Carbon mono-oxide
CO2 Carbon-di-oxide
HCHO Formaldehyde
TVOC Total volatile Organic compounds SO2 Sulphur-di-oxide
NO2 Nitrogen-di-oxide

BRIEF DESCRIPTION OF THE DRAWINGS

Next, some exemplary embodiments of the present invention are reviewed more closely with reference to the attached drawings, wherein.

DETAILED DESCRIPTION OF THE EMBODIMENTS

Indoor air quality is one of the top environmental health threats. There are several factors that determine the air quality and the air quality along with properties of the building determine building health index.

The parameters that provide a measure of building health index are:

Differential Pressure: Pressure is defined as the normal force per unit area of a surface. Pressure difference is a pressure difference between two spaces, for example indoor-outdoor, or indoor-indoor. Buildings are designed to maintain proper pressure difference.

Room temperature: It is defined as the range of indoor air temperatures, that is configured for indoor settings.

Carbon-di-oxide: Carbon-di-oxide ($CO_2$) is a byproduct of combustion, as well as a result of the metabolic process in living organisms. Because carbon dioxide is a result of human metabolism, concentrations within a building often are used to indicate whether adequate fresh air is being supplied to the space.

Other parameters that may be optionally configured to the system for later measurements are:

Humidity: Humidity represents the amount of water or moisture in the air.

Radon: Radon is a radioactive gas that is generated naturally in the soil and enters the house from the ground. Radon is one of the leading causes of lung cancer in many developed countries. Its concentration in buildings varies regionally and even locally.

TVOC: is defined as the total volatile organic compounds (TVOC) in indoor air. Correctly working building ventilation should ventilate compounds out of the building. High concentrations within a building might indicate failure in ventilation system or risk of high TVOC sources inside the building. High TVOC levels might cause sensory effects like sensory irritation, dryness, weak inflammatory irritation in eyes, nose, airways and skin.

Particulate matter: is the sum of all solid and liquid particles suspended in air. These particles vary greatly in size, composition, and origin. Particles are released in for example burning processes, traffic and industrial processes. When inhaled, some Particles can cause severe damage to the lungs and other organs. Correctly working building ventilation should filter Particles from the outside air. Concentrations within a building might indicate failure in ventilation system.

In addition, the building monitoring system can derive the active time: Depending on the room purpose, active time is defined differently. For example, when the room is occupied by humans, active time can be calculated from amount of $CO_2$ in the air. If the room is used as a cold storage, active time can be defined from temperature.

The sensors shall measure and collect the measurements for at least Carbon-di-oxide, room temperature and pressure differential and optionally any other additional parameters configured to be measured by the building monitoring system.

Figure 1:
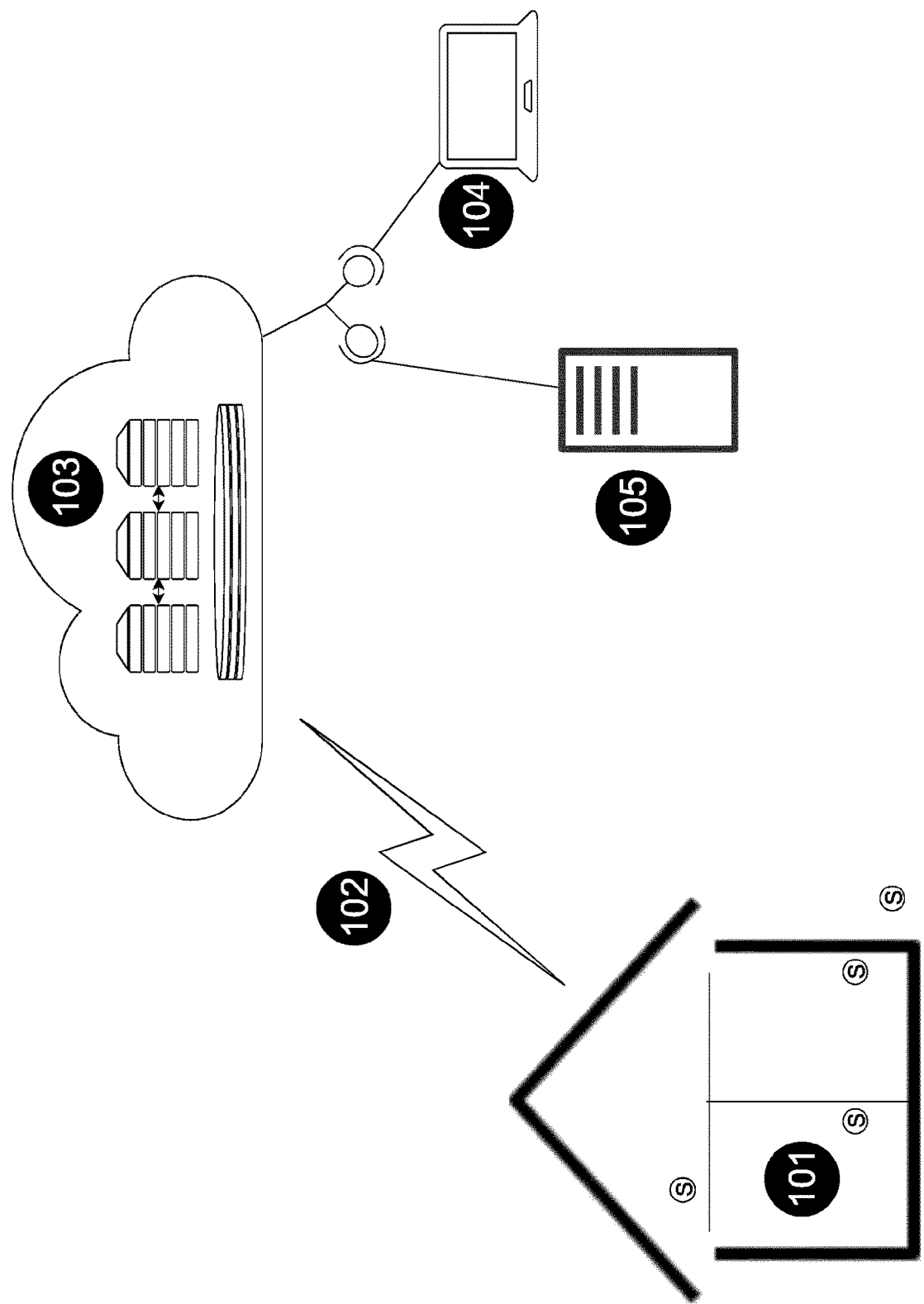
FIG. 1: illustrates the system architecture of the building monitoring system.

The system architecture of the building monitoring system in FIG. 1 comprises a building [101], a communication system [102], a central computational center, such as a server, terminal or other such computing entity, acting as an intelligent building monitoring system [103], a plurality of display devices where the health index is presented [104], and a computer where the health index is presented or used for further processing [105].

Figure 2:
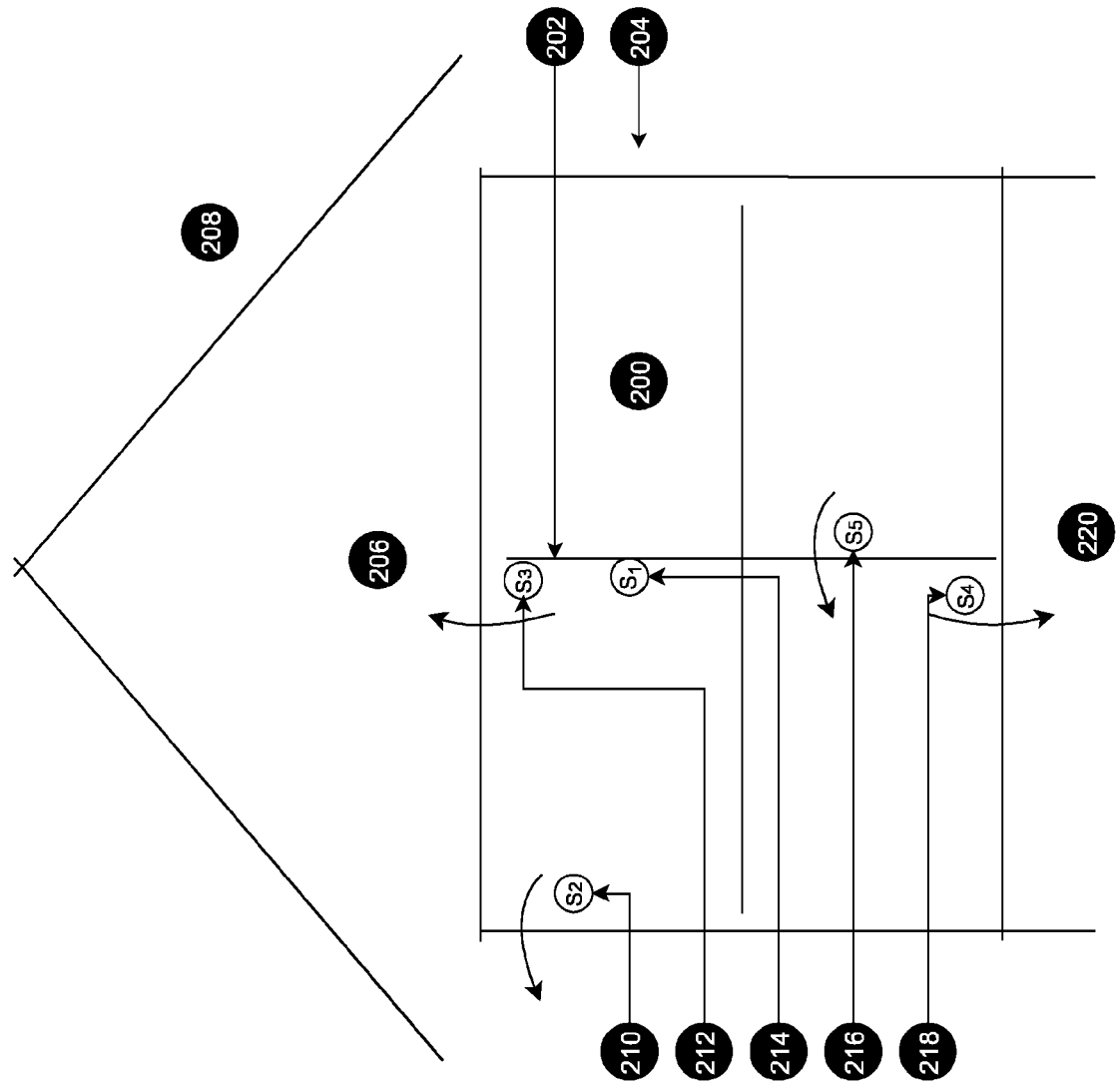
FIG. 2: illustrates the architecture of the building.

The detailed architecture of the building in FIG. 2 comprises plurality of rooms [200], in which each room can be one or more partitions including interior wall [202] or façade structure [204], the ceilings comprising interior side [206] and exterior side [208], where in the rooms may have sensor [210] installed at the interior side of one wall [204] to measure at least pressure differential through the façade structure, sensor [212] installed on another wall [204] in the building to measure one of the parameters configured to be measured by the building monitoring system, room sensor [214] installed in another wall [202] to measure same or a different parameter configured to be measured by the building monitoring system, sensor [216] installed in another wall [202] of the building to measure at least pressure differential between outside and inside walls of a room, sensor [218] installed to measure at least pressure differential between the outside [220] and inside floor of the room in the building.

Figure 3:
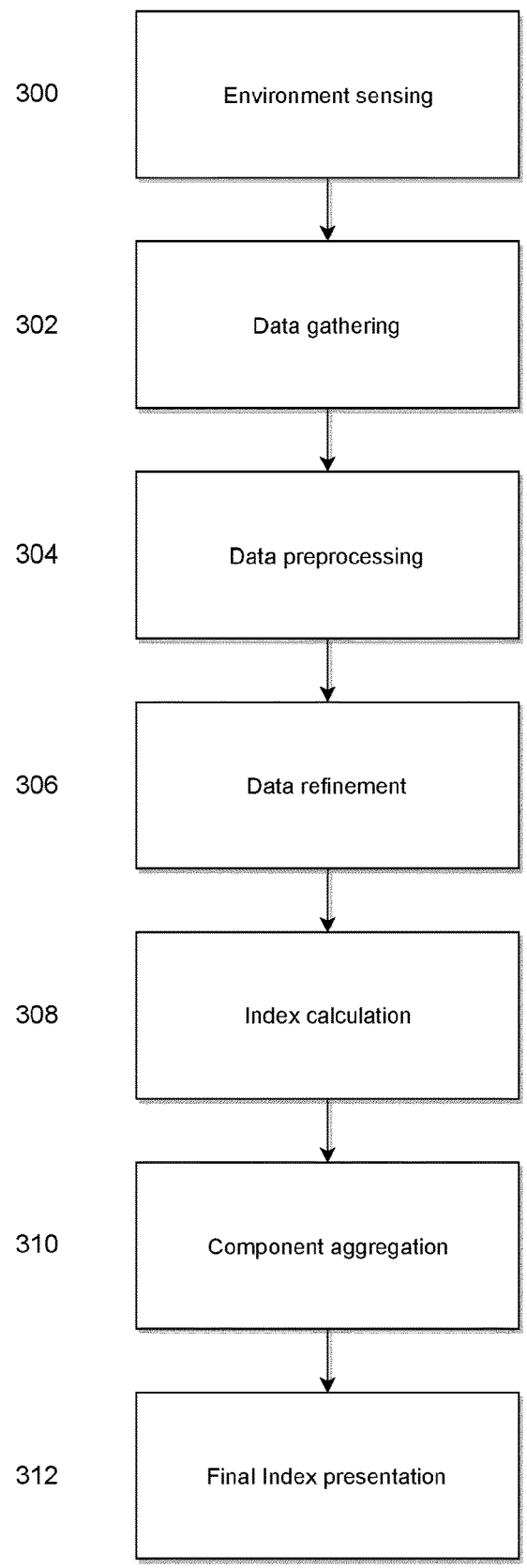
FIG. 3: illustrates the method for measuring building health index.

FIG. 3 illustrates the method in which at least one or more sensors may be installed inside a room of a building, where each of the sensors as shown in FIG. 2 may measure at least Carbon di-oxide, differential pressure and temperature, wherein the sensors may measure and store the values over a measurement period locally in the volatile memory in the sensors, and send it through a wireless communication system; wherein the data is pre-processed by the intelligent building monitoring system and refined for index calculation and then aggregated over a period of time to present the final index calculation and display over a plurality of the devices.

Figure 4:
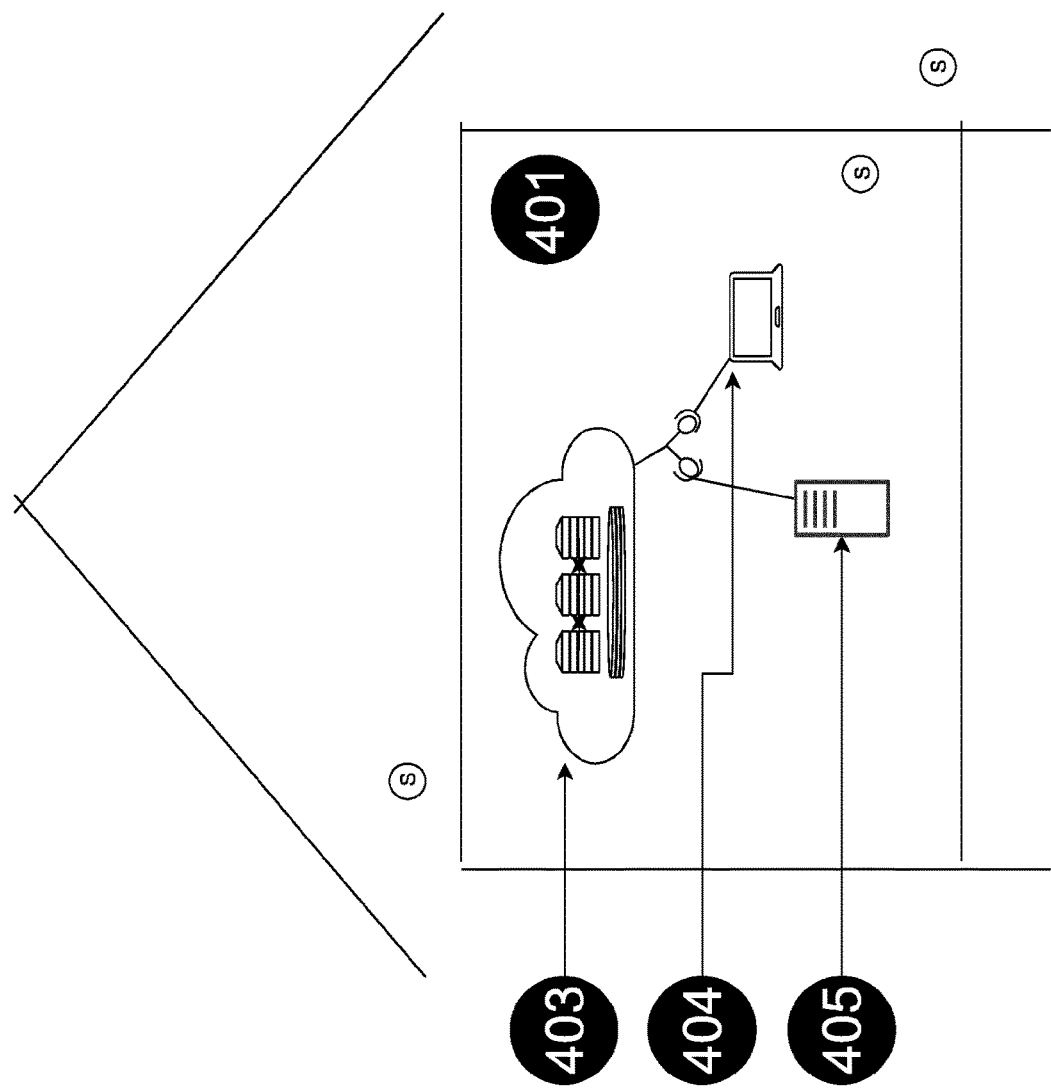
FIG. 4: illustrates the system architecture of the building monitoring system installed inside one building, which may be also installed in a plurality of buildings.

FIG. 4 illustrates another deployment of building monitoring system where the computation device, a plurality of display devices where the health index is presented [404] a computer where the health index is presented or used for further processing [405] may be installed inside the building or plurality of buildings [405], which is monitored remotely by such building monitoring system.

Figure 5:
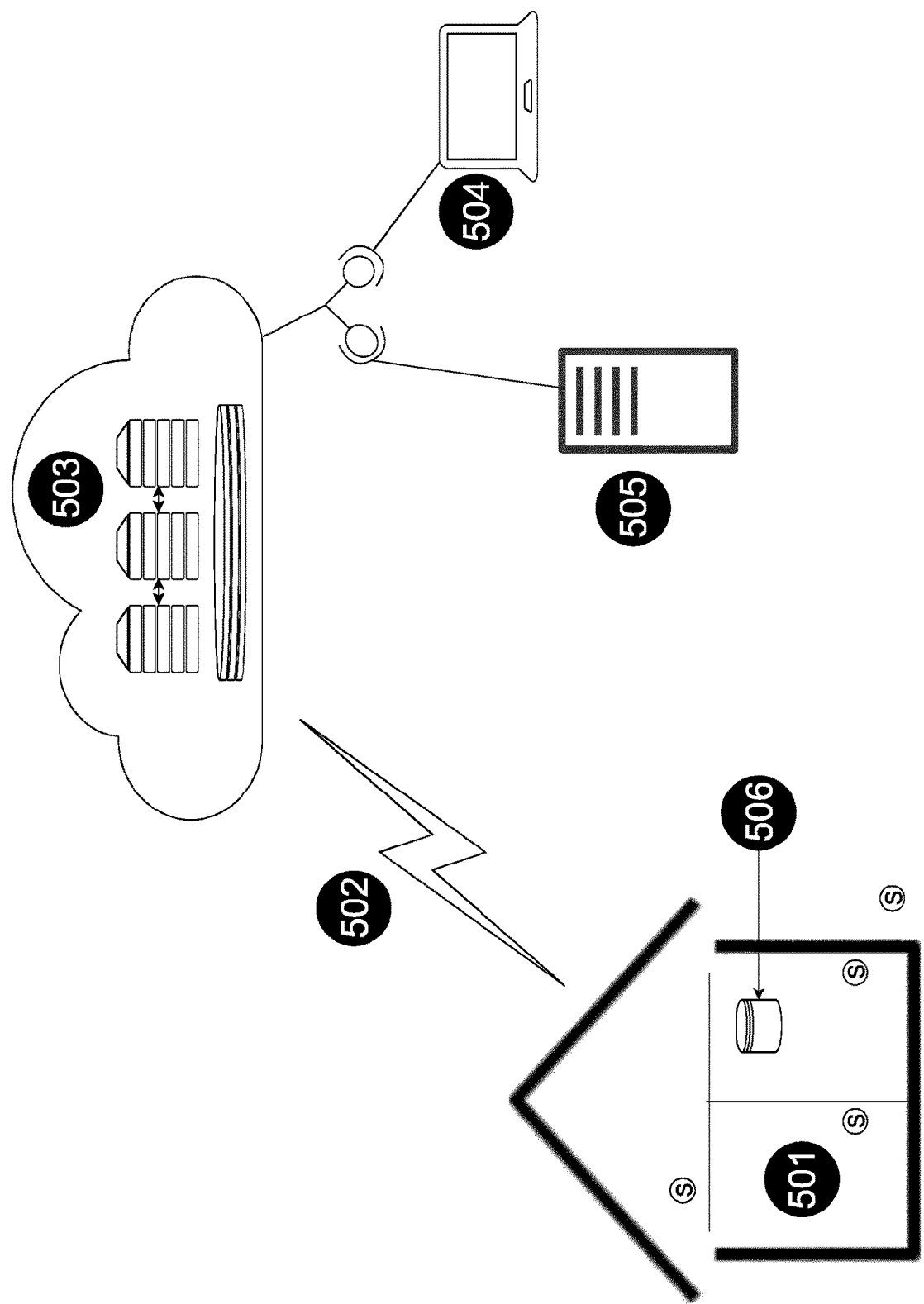
FIG. 5: illustrates another deployment of the building monitoring system where the sensors send the measurements to first a local computational device which sends the collected measurements to the intelligent building monitoring system.

FIG. 5 illustrates another deployment of building monitoring system where there may be one or a plurality of local gateways [506], which gateways [506] may receive measurements from the sensors installed in the building through a communication system and send it the building monitoring system for further processing.

The building monitoring system may be configured to know the context including at least one of the listed building locations, room type, active time of room when there are inhabitants or building specific technical details including either the ventilation type, covered area, heating type or some of them.

The building monitoring system may also use data from the users of the building when there are inhabitants, as an input parameter for usage when measuring the building health index. The input data from users could be about their feelings about temperature, humidity or other air quality related attributes that could be sensed qualitatively. The data from the users may be collected in a pre-defined format, configured by the building monitoring system.

The system preferably measures at least Pressure differential, temperature, CO2 at periodic intervals which is configured by the building monitoring system to the sensors, where CO2 measurements may also be used to determine the occupancy level of the building while other optional parameters e.g. particulate matters measurements may be additionally configured to be measured by the building monitoring system to check the air quality.

The system may determine and know the acceptable range of the parameters in relation to the external factors and calibration provided. Using that, it shall validate the measurements to find the time when one or more of the measurements are within or outside the acceptable range over a measurement period. For example co2 is in acceptable range when the measurements are below threshold value 950 ppm during the active time of the room or location. Threshold value may vary depending on the type of the location or room. Interpolation is done between measurement points to get accurate durations of acceptable ranges. Each of these validated ranges tell how long a period of time the measurements have been in the acceptable range and how long a period of time they have been outside the acceptable range.

A large set of such measurements over a longer period shall, give the information to the system to tell how the indoor air quality in the room of one or more buildings from where measurements were collected, is working as such. To find the building health index or one or more rooms in the building, the system may use methods like adding a weighted score to parameters in the range of 1-10 and use it to provide building health index.

Additionally, since the CO2 measurement is available, the system may be able to use the data from occupancy rate and acceptable range calibrated to the system to find if in certain time or period the system reaches alarming level and the ventilation mechanism or other tools to improve the building health index need to fine-tune.

The building health index and other individual measured parameters may provide information of how the building health is developing, how is the air quality and the intelligent building monitoring system may use the index to suggest change in the ventilation, pressure, temperature settings or flow or add/remove/modify one or more of the technical functions installed in the building to reach desired health index. The measurements and the building health index may be used for other purposes.

The method for measuring building health index comprises sensing the parameters from one or plurality of rooms from one or plurality of buildings [300], wherein each measured parameter is measured continuously or periodically by the sensors, and then the measured parameters are gathered by the building monitoring system [302] and pre-processed from raw measurement to get validated measurements of different parameters, wherein the resulting measurements [304], which may comprise refining the measurements by taking external factors influencing the measurements into account [306] and then aggregated to provide the individual index of each of the measured and validated measurements of the parameters [308], wherein each of the parameters individual index over similar measurement period could be aggregated with assigned weighted score, configured by the building monitoring system [310] resulting in building health index [312].

It is to be noted that the methods as described below, have shown steps being carried out in an order. However, it would be clear to a person skilled in the art that the order of the evaluation is immaterial with respect to the operation of the method. The ordering of steps as described herein is intended to not be limiting.

The scope of the invention is determined by the attached claims together with the equivalents thereof. The skilled persons will again appreciate the fact that the disclosed embodiments were constructed for illustrative purposes only, and the innovative fulcrum reviewed herein will cover further embodiments, embodiment combinations, variations and equivalents that better suit each particular use case of the invention.

The invention claimed is:

1. A method for measuring building health index comprising:

measuring, by one or more sensors installed inside of a building, a plurality of parameters that are recorded by the at least one or more sensors, one or more of the one or more sensors being configured to read values of the parameters and send the values over a network communication system to an intelligent building monitoring system the parameters comprising at least temperature, $CO_2$ and differential pressure, wherein the intelligent building monitoring system using the values over a measurement window in one indoor room and recording a number of instances the values of the parameters have been inside or outside an allowed pre-configured limit of the indoor room from where the measurement was taken, wherein the values are processed refined for index calculation by taking external factors into account that influence the one or more values and then collected over a period of time to obtain a building health index indicative of health of the building.

2. The method of claim 1, wherein the one or more sensors are configured to measure at least room temperature, $CO_2$, and differential pressure, wherein each of the sensors is configured to record additional parameters measured by the one or more sensors and configured in the building management system to be used for indoor air quality measurements.

3. The method of claim 2, further comprising displaying the building health index on a plurality of display devices or a computer, over a longer measurement period, the measurement period being an aggregation over days or weeks or months or a year in order to display the building health index over a longer period.

4. The method of claim 2, wherein measurements of multiple buildings over a time period are used to display an aggregation of an aggregate building health index of all the multiple buildings in a city, or a state or a country over one or more display devices.

5. The method of claim 1, wherein the one or more sensors are installed outside of at least one room in building or outside the building from where the one or more values are collected.

6. The method of claim 5, further comprising displaying the building health index on a plurality of display devices or a computer, over a longer measurement period, the measurement period being an aggregation over days or weeks or months or a year in order to display the building health index over a longer period.

7. The method of claim 5, wherein measurements of multiple buildings over a time period are used to display an aggregation of an aggregate building health index of all the multiple buildings in a city, or a state or a country over one or more display devices.

8. The method of claim 1, wherein the building monitoring system determines a layout, a type of the indoor room, a part of the building the indoor room is, a type of the building, an accurate location of one of the one or more sensors in the indoor room, and a level of the indoor room from the ground level.

9. The method of claim 8, further comprising displaying the building health index on a plurality of display devices or a computer, over a longer measurement period, the measurement period being an aggregation over days or weeks or months or a year in order to display the building health index over a longer period.

10. The method of claim 1, wherein some or all of the one or more sensors inside of the building are configured to store the one or more values inside the internal volatile memory of the sensors.

11. The method of claim 10, further comprising displaying the building health index on a plurality of display devices or a computer, over a longer measurement period, the measurement period being an aggregation over days or weeks or months or a year in order to display the building health index over a longer period.

12. The method of claim 1, further comprising recording at least one technical factor influencing air quality, wherein the at least one technical factor is configured to be recorded in the building monitoring system including at least one technical factor selected from a type of indoor room, a part of the building the indoor room is, a type of the building, accurate location of sensor in the indoor room, and a level of the indoor room from the ground level.

13. The method of claim 12, further comprising displaying the building health index on a plurality of display devices or a computer, over a longer measurement period, the measurement period being an aggregation over days or weeks or months or a year in order to display the building health index over a longer period.

14. The method of claim 1 wherein a computational device or a computer where the health index is presented or used for further processing is installed inside the building or a plurality of buildings in which one or more display devices for presentation of the values or the building health index are provided.

15. The method of claim 14, further comprising displaying the building health index on a plurality of display devices or a computer, over a longer measurement period, the measurement period being an aggregation over days or weeks or months or a year in order to display the building health index over a longer period.

16. The method of claim 1 wherein at least part of the one or more sensors is configured to send recorded one or more values to a computer device installed in the building which collects the values and sends the values over a wireless communication system to the central intelligent building monitoring system.

17. The method of claim 16, further comprising displaying the building health index on a plurality of display devices or a computer, over a longer measurement period, the measurement period being an aggregation over days or weeks or months or a year in order to display the building health index over a longer period.

18. The method of claim 1, further comprising displaying the building health index on a plurality of display devices or a computer, over a longer measurement period, the measurement period being an aggregation over days or weeks or months or a year in order to display the building health index over a longer period.

19. The method of claim 1, wherein measurements of multiple buildings over a time period are used to display an aggregation of building health index of all the multiple buildings in a city, or a state or a country over one or more display devices.

20. The method of claim 1, wherein the building health index and other individual measured parameters provide information as to how the health of the building is developing and the intelligent building monitoring system uses the building health index to suggest change in a ventilation, a pressure, temperature settings or a flow or add/remove/modify one or more technical functions installed in the building to reach a predetermined building health index.

* * * * *